United States Patent [19]

Arima et al.

[11] Patent Number: 5,168,155
[45] Date of Patent: Dec. 1, 1992

[54] COLOR MEASURING APPARATUS WITH FLASH LAMP COLOR TEMPERATURE MEASUREMENT

[75] Inventors: Jiro Arima; Naoyo Takata, both of Osaka, Japan

[73] Assignee: Minolta Camera Co., Ltd., Osaka, Japan

[21] Appl. No.: 632,052

[22] Filed: Dec. 21, 1990

[30] Foreign Application Priority Data

Dec. 28, 1989 [JP] Japan .................. 1-344511

[51] Int. Cl.$^5$ .................. G01J 3/50; G01N 21/25
[52] U.S. Cl. .................. 250/226; 356/405
[58] Field of Search .................. 250/226, 214 R; 356/405, 425, 402

[56] References Cited

U.S. PATENT DOCUMENTS

| | | | |
|---|---|---|---|
| 4,131,367 | 12/1978 | French et al. | 356/405 |
| 4,485,336 | 11/1984 | Yoshiyama et al. | 250/226 |
| 4,773,761 | 9/1988 | Sugiyama et al. | 356/405 |
| 4,989,982 | 2/1991 | Osaki et al. | 356/405 |
| 5,004,349 | 4/1991 | Sato et al. | 356/405 |

*Primary Examiner*—David C. Nelms
*Assistant Examiner*—Michael Messinger
*Attorney, Agent, or Firm*—Price, Gess & Ubell

[57] ABSTRACT

A measuring apparatus includes a flash tube for emitting flash light to a target in a first short period and a second short period, a detector for detecting amounts of light from the target in the flash light of the first short period and the flash light of the second short period, a receiver for receiving the flash light irrespective of the target to detect each reference light amount, an evaluator for evaluating the flash light according to the reference light amounts to generate a compensation signal for a characteristic of the flash light with respect to a characteristic of an ideal light source, and a calculator for calculating a characteristic value of the target under ideal light source according to the target light amount and the compensation signal.

8 Claims, 6 Drawing Sheets

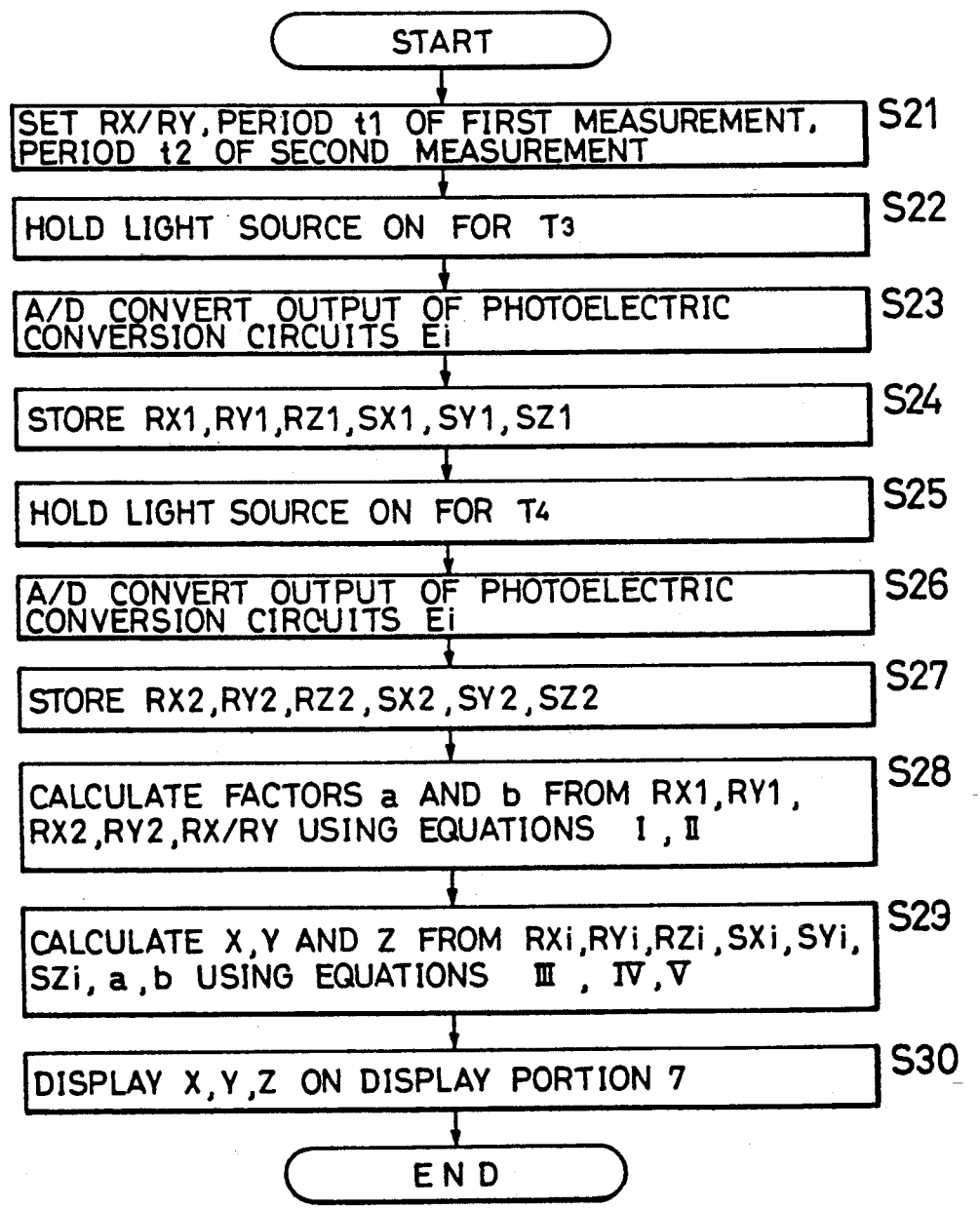

COLOR MEASURING APPARATUS WITH FLASH LAMP COLOR TEMPERATURE MEASUREMENT

BACKGROUND OF THE INVENTION

1. Field of the Invention

This invention relates to a measuring apparatus, particularly a measuring apparatus equipped with a light source for illuminating a target portion.

2. Description of Related Art

There have been a variety of measuring apparatus equipped with a light source. For example, there has been a colorimeter which is constructed so that a target portion is illuminated with white light of a certain luminous intensity, and light reflected from the target portion is measured to obtain tristimulus values of the reflected light. Such a colorimeter is liable to give different measurement values depending on color temperatures of the light source. Accordingly, it is necessary to maintain the light source at a constant color temperature.

For example, color temperature of light which is emitted by a xenon flash lamp (hereinafter referred to as Xe tube) used as a light source of the colorimeter varies with the flash tube current which flows in the Xe tube when it flashes. The flash tube current is supplied from a charged main capacitor. The flash tube current is determined by the circuit impedance of a discharge loop, including the Xe tube, and the voltage applied across the Xe tube at the time of flashing. The impedance of the Xe tube is determined by its internal gas pressure and electrode spacing. Xe tubes have their respective specific impedance values, which vary with their temperatures. Therefore, the flash tube current varies with the lapse of time during a discharge process even when the lighting source voltage is kept constant. Furthermore, color temperature of the flash tube cannot be maintained at a constant level even when flashing is repeated at relatively short intervals. It is therefore difficult to maintain the light source at a constant color temperature when using a discharge lamp as the light source.

When using another type of light source, for example, an incandescent lamp, the color temperature rises until it reaches a specific level after the lamp is turned on. In this case, the rising speed and peak level of color temperature are subject to change with time even if the applied voltage is controlled to a fixed value. When the lamp is lit by a pulse voltage, color temperature also changes with variations in pulse duration.

Accordingly, in such measuring apparatus equipped with a light source for illuminating a target portion, it is very difficult to completely obtain a constant color temperature in each lighting process. Consequently, the measurement accuracy is lowered due to slight variations in color temperature.

It is an object of the present invention to provide a measuring apparatus which has overcome the above-mentioned drawbacks, and makes it possible to eliminate color temperature variations of the light source from influencing the measurement.

SUMMARY OF THE INVENTION

A measuring apparatus of the present invention comprises a light source, a light source detector for detecting light from the light source to generate an electrical charge, an integrator for integrating the electrical charge generated by the detector, a controller for controlling the integrator so as to integrate the electrical charge in two different time periods, and a calculator for calculating compensation data for a characteristic of the light source with respect to a characteristic of an ideal light source according to the respective two integrated electrical charges of the two different time periods.

Another measuring apparatus of the present invention comprises means for emitting light to provide a light source, means for receiving the light to generate an electrical charge according to intesity of the light, means for controlling the receiving means so as to permit the generated electrical charge to integrate in two different time periods, and means for calculating compensation data for a characteristic of the light source with respect to a characteristic of an ideal light source according to the respective two integrated electrical charges of the two different time periods.

Another measuring apparatus of the present invention comprises a flash tube for emitting flash light to a target in a first short period and a second short period, means for detecting amounts of light from the target in the flash light of the first short period and the flash light of the second short period, means for receiving the flash light irrespective of the target to detect each reference light amount, means for evaluating the flash light according to the reference light amounts to generate a compensation signal for a characterisstic of the flash light with respect to a characteristic of an ideal light source, and means for calculating a characteristic value of the target under an ideal light source according to the target light amount and the compensation signal.

According to the present invention, direct light from the light source is detected at two different color temperatures so that compensation data for a characteristic of the light source with respect to a characteristic of an ideal light source is calculated according to the two different data. Raw measurement data of the target illuminated by the light source are corrected by the compensation data to provide measurement values of the target on condition that the color temperature of the light source is a specific constant value. Accordingly, the present invention makes it possible to get rid of the effect of color temperature variations of the light source from measurement data, resulting in a significant improvement of measurement accuracy.

This and other objects features and advantages of the present invention will become more apparent upon a reading of the following detailed description with reference to accompanying drawings.

BRIEF DESCRIPTION OF THE DRAWINGS

FIG. 6 is a flow chart showing operational steps executed in the second embodiment.

DETAILED DESCRIPTION OF PREFERRED EMBODIMENTS OF THE INVENTION

Figure 1:
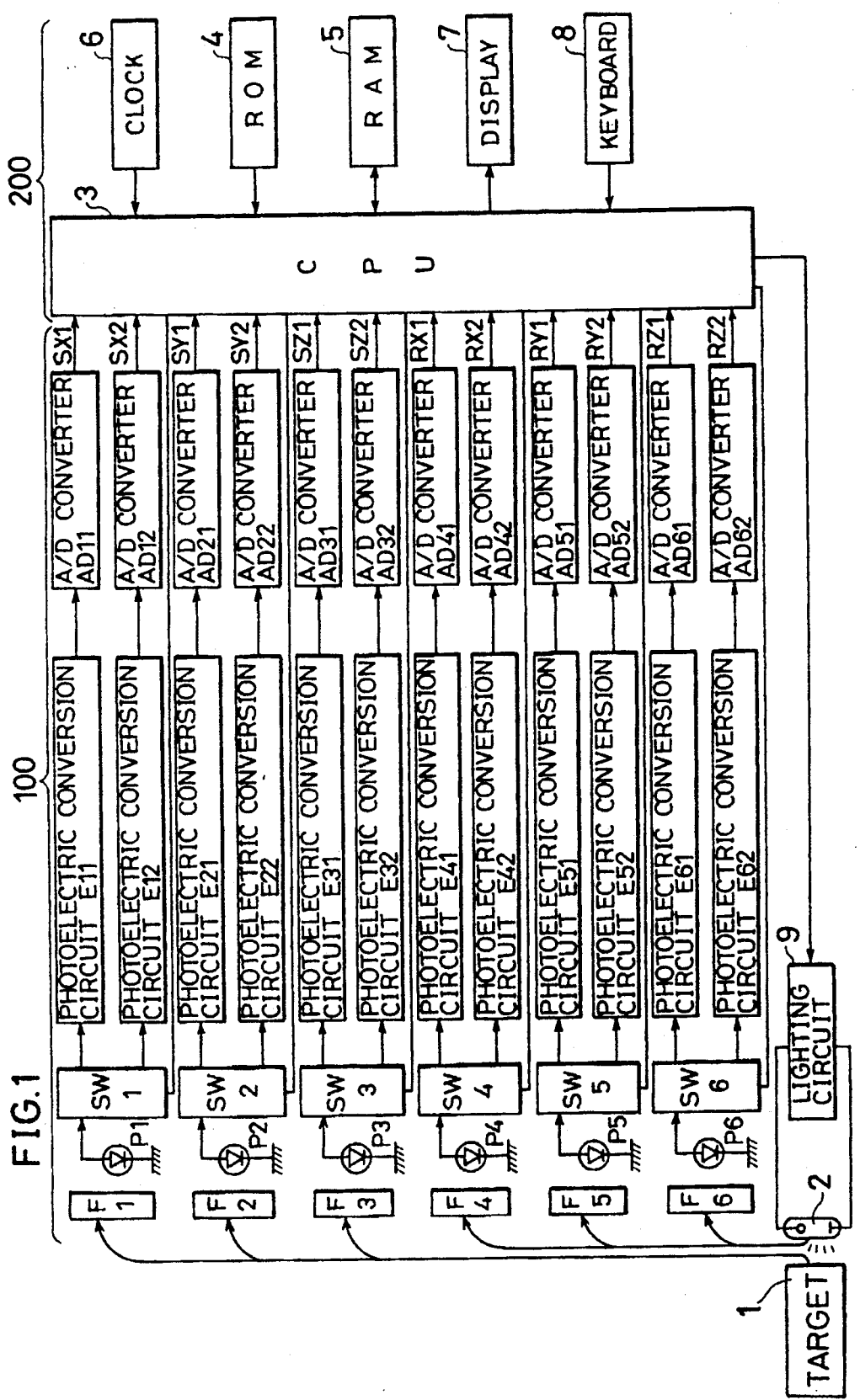
FIG. 1 is a block diagram showing an overall construction of a first embodiment of the present invention.

FIG. 1 schematically shows an overall construction of a colorimeter, a preferred first embodiment of the present invention. This colorimeter consists essentially of two portions, a photoelectric conversion portion 100 and a data processing portion 200, as shown in FIG. 1. The photoelectric conversion portion 100 includes six photodiodes P1-P6 for converting light into electric charge. Three photodiodes P1-P3 of the six photodiodes P1-P6 are used to measure reflected light from a target portion 1 while the remaining three photodiodes P4-P6 are used to measure (or monitor) direct light from a light source 2.

Combinations of spectral sensitivities of the photodiodes P1-P3 and spectral transmittances of filters F1-F3 provided in front of the respective photodiodes P1-P3 are arranged so that spectral characteristics of their light outputs can have spectral sensitivities approximately corresponding to CIE color matching functions $x(\lambda)$, $y(\lambda)$ and $z(\lambda)$, respectively. The photodiodes P4-P6 and filters F4-F6 are also arranged in a similar way.

In the photoelectric conversion portion 100, the photodiodes P1-P6 detect reflected light from the target portion 1 and direct light from the light source 2 through the filters F1-F6, and signal change-over switches SW1-SW6 change over respective outputs of the photodiodes P1-P6. The outputs are integrated by photoelectric conversion circuits E11, E21, E31, E41, E51 and E61 for a first period of the lighting time. Also, the outputs are integrated by photoelectric conversion circuits E12, E22, E32, E42, E52 and E62 for a second period of the lighting time. Finally, integrated outputs are converted into digital signals by A/D converters AD11-AD62 to obtain raw data SX1, SX2, SY1, SZ1, SZ2, RX1, RX2, RY1, RY2, RZ1 and RZ2, wherein the letter S represents measuring light reflected from the target portion 1, the letter R represents reference light transmitted directly from the light source 2, the letter X represents x degrees on the color co-ordinate, the letter Y represents y degrees, the letter Z represents z degrees, the number 1 represents the first period of the lighting time, and the number 2 represents the second period of the lighting time.

From the raw data, the data processing portion 200 calculates measurement values of the target portion 1 corresponding to CIE color matching functions $x(\lambda)$, $y(\lambda)$ and $z(\lambda)$ on condition that the color temperature of the light source 2 is a specific constant value. The data processing portion 200 includes a microcomputer 3 for performing control and calculation, a read only memory 4 (ROM) which holds programs for system control, color conversion, etc., a random access memory (RAM) 5 for storing color information, or relationship between the flash lighting time and color temperature of the Xe tube, a display portion 7 including an LCD display or a printer for showing the result of measurement, and a keyboard 8 for operating the colorimeter. A xenon flash lamp (Xe tube) is used for the light source 2. The Xe tube is connected with a lighting circuit 9 which is in turn connected with the microcomputer 3.

Figure 2:
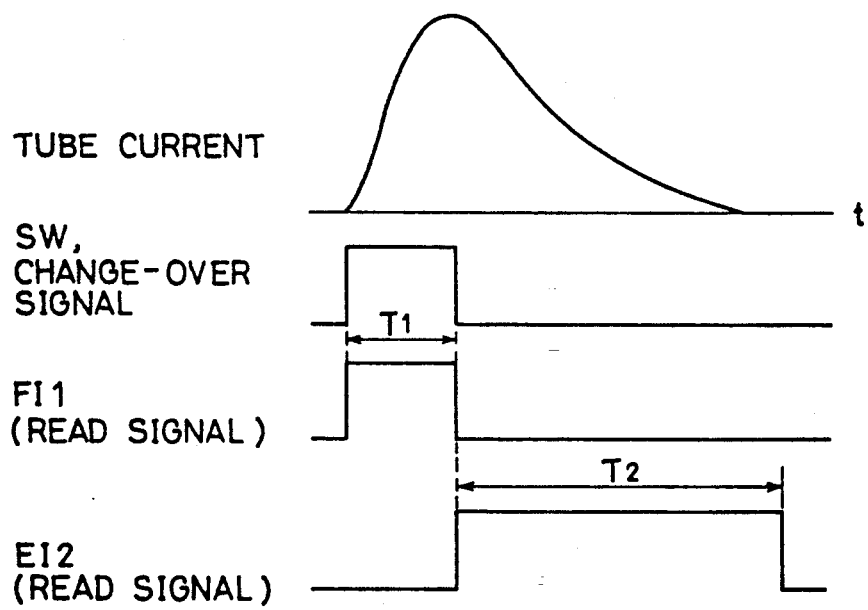
FIG. 2 is a signal timing chart showing a relationship between signals generated in the first embodiment.

FIG. 2 is a timing chart illustrating tube current flowing in the Xe tube and a change-over control signal for changing over the first measuring period T1 and the second measuring period T2. The tube current has a property of rising in an early time and falling after the lapse of some time. The signal change-over switches SW1-SW16 are operated in such a way that the measuring circuits for the first measuring period is changed to the measuring circuits for the second measuring period coincides with the peak of the tube current, and the second measuring period T2 is longer than the first measuring period T1 to provide perdetermined measuring times.

Also, the light source 2 has a property that an averaged color temperature of the first period of the lighting time is higher than that of the second period of the lighting time. Accordingly, a constant color temperature value for the light source 2 can be obtained by executing an appropriate weighted average calculation of two raw data obtained in the first measuring period and the second measuring period.

A specific constant color temperature of the light source 2 is provisionally set in accordance with a value $RXi/RYi$ derived from two raw data obtained by measuring direct light from the light source 2 in the first measuring period and the second measuring period. It should be noted that the suffix i represents which measuring period of the lighting time, more specifically, i=1 represents the first measuring period, and i=2 represents the second measuring period. Also, the more reddish the light from the light source 2, the lower its color temperature. Accordingly, it could be seen that larger values of $RXi/RYi$ indicated lower color temperatures.

The following explanation describes a calculation that from the raw data obtained in the first and second measuring periods of the lighting time, measurement values of the target portion 1 are calculated on the condition that the color temperature of the light source 2 is a specific color temperature RX/RY. First, weight factors a, b for the raw data of the first and second measuring periods of the lighting time are obtained. These weight factors are used to correct the raw data of the target portion 1 based on the condition that the color temperature of the light source is the specific color temperature of RX/RY as follows.

$$a(RX1/RY1)+b(RX2/RY2)=RX/RY \qquad \text{I}$$

$$a+b=1 \qquad \text{II}$$

Here, a and b given by Equations I and II indicate weight factors by which the raw data of the first and second measuring periods are multiplied to produce the color temperature RX/Ry of the light source 2. Accordingly, the raw data of the light reflected from the target portion 1 are processed by the following Equations to calculate values X, Y and Z, respectively:

$$a(SX1/RX1)+b(SX2/RX2)=X \qquad \text{III}$$

$$a(SY1/RY1)+b(SY2/RY2)=Y \qquad \text{IV}$$

$$a(SZ1/RZ1)+b(SZ2/RZ2)=Z \qquad \text{V}$$

The values X, Y and Z obtained by the above Equations represent CIE tristimulus values of the target portion 1 on the condition that the color temperature of the light source 2 is expressed by RX/RY. Consequently, it is possible to obtain color measurement values of the target portion 1 at the constant color temperature of the light source 2 in spite of variations in actual color temperature of the light source 2.

Figure 3:
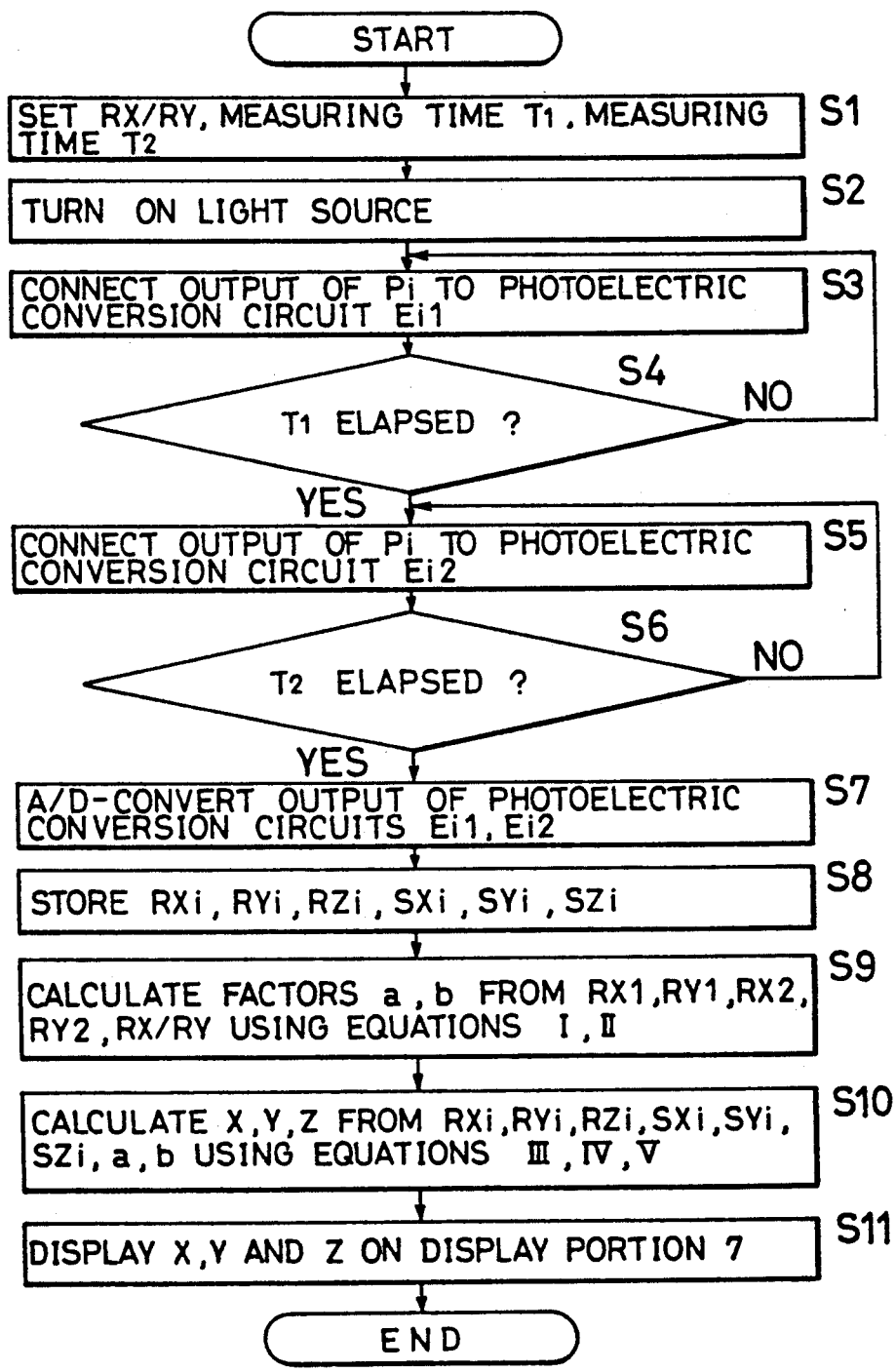
FIG. 3 is a flow chart showing operational steps executed in the first embodiment.

Next, the above calculation will be described with reference to the flow chart of FIG. 3. Before starting measurement, in Step S1, the specific constant color temperature value RX/RY of the light source 2, first measuring time T1, and second measuring time T2 of the lighting time are set and stored in RAM 5. The light source (Xe tube) 2 is turned on in Step S2. In Step S3, output of each photodiode Pi transferred to the photoelectric conversion circuit Ei1 (i=1 to 6).

Subsequently, this routine proceeds to Step S4 in which it is discriminated whether the preset period T1 has elapsed. If the preset period T1 has not elapsed yet, this routine returns to Step S3. When the preset period T1 has elapsed, this routine proceeds to Step S5 in which the signal change-over switch SWi is operated to transfer the output of the photodiode Pi to the photoelectric conversion circuit Ei2.

Next, the routine proceeds to Step S6 in which it is discriminated whether the preset period T2 has elapsed after transferring the output of the photodiode Pi to the photoelectric conversion circuit Ei2. If the preset period T2 has not elapsed yet, this routine returns to step S5. When the preset period T2 has elapsed, this routine proceeds to Step S7 in which the output signals of the photoelectric conversion circuits Ei1 and Ei2 are A/D-converted. Then, in Step S8, the values RXi, RYi, RZi, SXi, SYi and SZi obtained by A/D-conversion of the outputs of each pair of photoelectric conversion circuits Ei1 and Ei2 are stored in RAM 5. Subsequently, in Step S9, factors a, b of Equation I are calculated in accordance with Equations I and II using the values RX1 and RY1, RX2, RY2 and RX/RY stored in RAM 5, and in Step S10, X, Y and Z are calculated in accordance with Equations III, IV and V using the values RXi, RYi, RZi, SXi, SYi, SZi, a, b stored in RAM 5. Finally, the calculated values X, Y and Z are displayed on the display portion 7 in Step S11.

In the first embodiment, light measurement is performed in the first and second measuring periods of one lighting time. However, it should be noted that the present invention is not limited in the first embodiment, and may take other constructions as far as light measurement data can be obtained at different color temperatures. For example, it is possible to obtain light measurement data at different color temperatures by integrating outputs in a short period and a long period. This is because an average color temperature value becomes lower in a longer integral time owing to the increased effect of the latter portion of the lighting time where the color temperature is low.

In the first embodiment, a single flash of the light source 2 is divided into the first and second measuring periods of the lighting time to obtain two different data, and a constant color temperature of the light source 2 is calculated from the two different data. However, instead of dividing the lighting time into the first and second measuring periods, it is possible to accomplish light measurement of a light source with two discrete flashes having different lighting times. In this case, the longer the lighting time, the lower the average color temperature. Accordingly, a similar result can be achieved by using two different measurement data obtained from short and long flashes.

Figure 4:
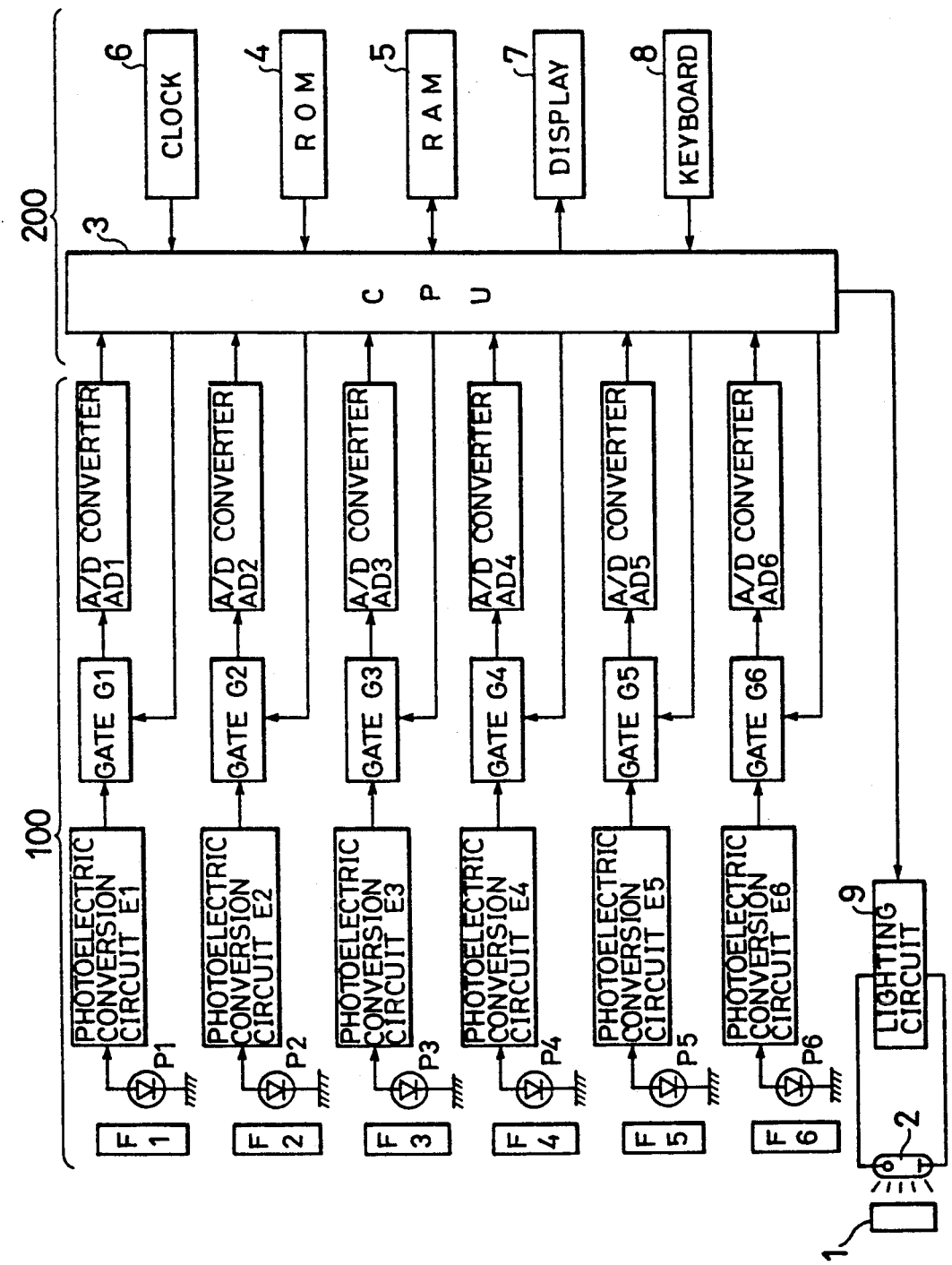
FIG. 4 is a block diagram showing a second embodiment of the present invention.
Figure 5:
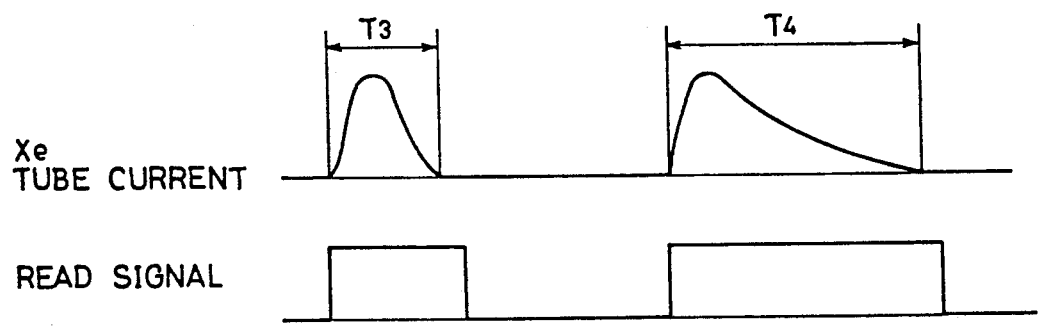
FIG. 5 is a signal timing chart showing a relationship between signals generated in the second embodiment.

FIG. 4 is a block diagram showing a second embodiment of the present invention which is intended to obtain measurement values on the condition that the color temperature of the light source is a specific constant value by measuring short and long flashes of light. In the first embodiment illustrated in FIG. 1, each photodiode Pi is associated with a pair of photoelectric conversion circuits Ei1 and Ei2 and a pair of A/D-converters ADi1 and ADi2. However, in the second embodiment, each photodiode Pi is associated with one each photoelectric conversion circuit Ei and A/D-converter ADi. FIG. 5 is a timing chart showing a relationship between signals generated in the second embodiment.

Operational steps of the second embodiment will be described with reference to the flow chart of FIG. 6. Before starting measurements, in Step S21, a specific constant color temperature value RX/RY of the light source 2, first measuring period T3, and second measuring period T4 are set and stored in RAM 5. The light source (Xe tube) 2 is turned on for the measuring period T3 in Step S22, and in Step S23 output of each photoelectric conversion circuit Ei is A/D-converted. Subsequently, in Step S24, the values RX1, RY1, RZ1, SX1, SY1 and SZ1 obtained by A/D-conversion of the output of each photoelectric conversion circuit Ei are stored in RAM 5.

Next, in Step S25, the light source (Xe tube) 2 is turned on for the measuring period T4, and in Step S26 output of each photoelectric conversion circuit Ei is A/D-converted. In Step S27, the values RX2, RY2, RZ2, SX2, SY2 and SZ2 obtained by A/D-conversion of the output of each photoelectric conversion circuit Ei are stored in RAM 5. Factors a, b of Equation I are calculated in accordance with Equations I and II using the values RX1, RY1, RX2, RY2 AND RX/RY stored in RAM 5 is Step S28. Thereafter, in Step S29, X, Y and Z are calculated in accordance with Equations III, IV and V using the values RXi, RYi, RZi, SXi, SZi, a, b stored in RAM 5. Finally, the calculated values X, Y and Z are displayed on the display portion 7 in Step S30.

Although a flash lamp is used as the light source in the second embodiment, it is also possible to use a steady state light source like a halogen lamp for lighting. The same effect as the flash lamp can be obtained in such steady state light source. The tube current is adjusted by means of pulse control so as to emit light of two different color temperatures, so that two measurement data can be obtained at different color temperatures of the light source.

As an example, by using the same construction as FIG. 1, integration of luminous intensity of the halogen lamp up to its luminous peak gives data at a low color temperature while integration of luminous intensity of the halogen lamp after its luminous peak gives a data at a high color temperature.

Also, by using the construction of FIG. 4, measurement data obtained in short and long measuring periods of lighting give data at low and high color temperatures respectively. Therefore, with either circuit construction, it is possible to obtain measurement values of a target portion on the condition that the color temperature of the light source is a specific constant value as the above-mentioned embodiments.

Also, when the lamp is turned on in pulses, light measurement data obtained from pulses of a low duty ratio provides data at a low color temperature while light measurement data obtained from pulses of a high duty ratio provides data at a high color temperature. Therefore, it is also possible to obtain measurement values of a target portion on the condition that the color temperature of the light source is a specific constant value as the above-mentioned embodiements.

Further, it is possible to provide two different data, i.e., data at a high voltage and data at a low voltage, by varying the voltage of the lighting source voltage.

Moreover, the present invention has been described with reference to colorimeters, it is to be understood that the present invention can be executed in other measuring apparatus, such as a spectrometer.

Although the present invention has been fully described by way of example with reference to the accompanying drawings, it should be understood that various changes and modifications will be apparent to those skilled in the art. Therefore, unless otherwise such changes and modifications depart from the scope of the invention, they should be construed as being included therein.

What is claimed is:

1. A measuring apparatus comprising:
    a flash lamp;
    first photoelectric conversion means for receiving light from said flash lamp and converting the light to a first electrical signal in accordance with the intensity of the light;
    time dividing means for dividing a duration during which said flash lamp emits the light into a plurality of time periods;
    means for measuring color temperatures of said flash lamp in the plurality of time periods respectively based on the first electrical signal, and
    means for calculating compensation data to compensate for a variation of the color temperature of said flash lamp based on the measured color temperatures.

2. A measuring apparatus as claimed in claim 1, further comprising:
    conducting means for conducting light from said flash lamp to a target;
    second photoelectric conversion means for receiving light from the target and converting the light to a second electrical signal in accordance with the intensity of the light;
    producing means for producing third electrical signals based on the second electrical signal, said third electrical signals corresponding to the intensity of the light from the target in the plurality of time periods respectively, and
    correction means for correcting the second electrical signal based on the compensation data and the third electrical signals so as to provide a measurement to be obtained when a target is measured under an ideal flash lamp.

3. A measuring apparatus comprising:
    a flash lamp;
    first photoelectric conversion means for receiving light from said flash lamp and converting the light to a first electrical signal in accordance with the intensity of the light;
    control means for controlling the flash lamp so as to emit light in a plurality of time periods whose durations are different from one another;
    means for measuring color temperatures of said flash lamp in the plurality of different emitting time periods respectively based on the first electrical signal, and
    means for calculating compensation data to compensate for a variation of the color temperature of said flash lamp based on the measured color temperatures.

4. A measuring apparatus as claimed in claim 3, further comprising:
    conduction means for conduction light from said flash lamp to a target;
    second photoelectric conversion means for receiving light from the target and converting the light to a second electrical signal in accordance with the intensity of the light;
    producing means for producing third electrical signals based on the second electrical signal, said third electrical signals corresponding to the intensity of the light from the target in the plurality of different emitting time periods respectively, and
    correction means for correcting the second electrical signal based on the compensation data and the third electrical signal so as to provide a measurement to be obtained when a target is measured under a predetermined ideal flash lamp.

5. An apparatus for measuring a characteristic of a target optically comprising:
    a flash lamp for illuminating a target;
    first photoelectric conversion means for receiving light from said flash lamp directly and converting the light to a first electrical signal in accordance with the intensity of the light;
    second photoelectric conversion means for receiving light from the target and converting the light to a second electrical signal in accordance with the intensity of the light;
    time dividing means for dividing a duration during which said flash lamp emits the light into a plurality of time periods;
    means for measuring color temperatures of said flash lamp in the plurality of time periods respectively based on the first electrical signal;
    means for measuring light intensities of the light from the target in the plurality of time periods respectively based on the second electrical signal, and
    correction means for correcting the second electrical signal based on the color tempertures and the light intensities measured in the plurality of time periods so as to provide a measurement to be obtained when the target is measured under an ideal flash lamp whose light has a predetermined color temperature.

6. An apparatus for measuring a characteristic of a target optically comprising:
    a flash lamp for illuminating a target;
    first photoelectric conversion means for receiving light from said flash lamp directly and converting the light to a first electrical signal in accordance with the intensity of the light;
    second photoelectric conversion means for receiving light from the target and converting the light to a second electrical signal in accordance with the intensity of the light;
    control means for controlling the flash lamp so as to emit light in a plurality of time periods whose durations are different from one another;
    means for measuring color temperatures of said flash lamp in the plurality of different emitting time periods respectively based on the first electrical signal;
    means for measuring light intensities of the light from the target in the plurality of different emitting time periods respectively based on the second electrical signal, and correction means for correcting the second electrical signal based on the color temperatures and the light intensities measured in the plurality of different emitting time periods so as to provide a measurement to be obtained when the target is measured under an ideal flash lamp whose light has a predetermined color temperature.

7. A light monitoring system to correct for variations in color temperature of a light source comprising:

a light source providing emitted light of at least two different color temperatures during a light emission cycle towards a target object;

means for measuring the emitted light during at least two separate time periods that are each respectively of a shorter time period than the light emission cycle, each time period corresponding to a different color temperature and providing at least two separate signals representative of the different color temperatures of the light source during the light emission cycle;

means for measuring light reflected from a target object during the light emission cycle and providing an output signal, and means for correcting the output signal in accordance with the two separate color temperature signals.

8. The light monitoring system of claim 7 wherein the light source is a flash lamp.

* * * * *